US008033120B2

(12) United States Patent
Singh et al.

(10) Patent No.: US 8,033,120 B2
(45) Date of Patent: *Oct. 11, 2011

(54) COMPOSITIONS AND METHODS CONTAINING FLUORINE SUBSTITUTED OLEFINS

(75) Inventors: Rajiv R. Singh, Getzville, NY (US); Hang T. Pham, Amherst, NY (US); David P. Wilson, East Amherst, NY (US); Raymond H. Thomas, Pendleton, NY (US); Ian Shankland, Randolph, NJ (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/426,948

(22) Filed: Apr. 20, 2009

(65) Prior Publication Data

US 2009/0302285 A1    Dec. 10, 2009

Related U.S. Application Data

(60) Continuation-in-part of application No. 11/385,259, filed on Mar. 20, 2006, which is a division of application No. 10/694,273, filed on Oct. 27, 2003, now Pat. No. 7,534,366, and a continuation-in-part of application No. 10/695,212, filed on Oct. 27, 2003, now abandoned, and a continuation-in-part of application No. 10/694,272, filed on Oct. 27, 2003, now Pat. No. 7,230,146.

(60) Provisional application No. 60/421,263, filed on Oct. 25, 2002, provisional application No. 60/421,435, filed on Oct. 25, 2002.

(51) Int. Cl.
*C09K 5/04* (2006.01)

(52) U.S. Cl. .................... 62/6; 252/67; 252/71; 252/75; 252/78.1

(58) Field of Classification Search .................... 252/67, 252/71, 75, 78.1; 62/6
See application file for complete search history.

(56) References Cited

U.S. PATENT DOCUMENTS

| | | | |
|---|---|---|---|
| 2,846,458 A | 8/1958 | Haluska |
| 2,834,748 A | 10/1958 | Bailey et al. |
| 2,889,379 A | 6/1959 | Ruh et al. |
| 2,917,480 A | 12/1959 | Bailey et al. |
| 2,931,840 A | 4/1960 | Maley |
| 2,970,988 A | 2/1961 | Lo |
| 2,996,555 A | 8/1961 | Rausch |
| 3,085,065 A | 4/1963 | Kvalnes |
| 3,085,918 A | 4/1963 | Sherliker et al. |
| 3,472,826 A | 10/1969 | Potts et al. |
| 3,659,023 A | 4/1972 | Regan |
| 3,723,318 A | 3/1973 | Butler et al. |
| 3,884,828 A | 5/1975 | Butler et al. |
| 4,465,786 A | 8/1984 | Zimmer et al. |
| 4,650,914 A | 3/1987 | Woodard et al. |
| 4,755,316 A | 7/1988 | Magid et al. |
| 4,788,352 A | 11/1988 | Smutny |
| 4,798,818 A | 1/1989 | Baizer et al. |
| 4,900,874 A | 2/1990 | Ihara et al. |
| 4,944,890 A | 7/1990 | Deeb et al. |
| 4,945,119 A | 7/1990 | Smits et al. |
| 4,971,212 A | 11/1990 | Gorski et al. |
| 4,975,212 A | 12/1990 | Thomas et al. |
| 5,008,028 A | 4/1991 | Jolley et al. |
| 5,155,082 A | 10/1992 | Tung et al. |
| 5,182,040 A | 1/1993 | Bartlett et al. |
| 5,250,208 A | 10/1993 | Merchant et al. |
| 5,254,280 A | 10/1993 | Thomas et al. |
| 5,370,812 A | 12/1994 | Brown |
| 5,532,419 A | 7/1996 | Van Der Puy et al. |
| 5,545,777 A | 8/1996 | Morikawa et al. |
| 5,574,192 A | 11/1996 | Van der Puy et al. |
| 5,578,137 A | 11/1996 | Shealy et al. |
| 5,611,210 A | 3/1997 | Nimitz et al. |
| 5,616,275 A | 4/1997 | Chisolm et al. |
| 5,648,017 A | 7/1997 | Bartlett et al. |
| 5,674,451 A | 10/1997 | Nimitz et al. |
| 5,679,875 A | 10/1997 | Aoyama et al. |
| 5,710,352 A | 1/1998 | Tung |
| 5,714,083 A | 2/1998 | Turner et al. |
| 5,728,904 A | 3/1998 | Van der Puy et al. |
| 5,736,062 A | 4/1998 | Basile |
| 5,736,063 A | 4/1998 | Richard et al. |
| 5,744,052 A | 4/1998 | Bivens |
| 5,763,063 A | 6/1998 | Pass et al. |
| 5,788,886 A | 8/1998 | Minor et al. |
| 5,792,383 A | 8/1998 | Reyes-Gavilan et al. |
| 5,800,730 A | 9/1998 | Bivens et al. |
| 5,811,603 A | 9/1998 | Elsheikh |
| 5,866,030 A | 2/1999 | Reyes-Gavilan et al. |

(Continued)

FOREIGN PATENT DOCUMENTS

EP    0398147    11/1990

(Continued)

OTHER PUBLICATIONS

Translation of JP 04110388 submitted in U.S. Appl. No. 10/694,273 Nov. 10, 2008.*

(Continued)

*Primary Examiner* — Amina Khan
(74) *Attorney, Agent, or Firm* — Colleen D. Szuch

(57) ABSTRACT

The use of pentafluoropropene (HFO-1225) and tetrafluoropropene (HFO-1234) in refrigeration equipment is disclosed. These materials are generally useful as refrigerants for heating and cooling, as blowing agents, as aerosol propellants, as solvent composition, and as fire extinguishing and suppressing agents.

21 Claims, No Drawings

U.S. PATENT DOCUMENTS

| Patent No. | Kind | Date | Inventor | Ref |
|---|---|---|---|---|
| 5,969,188 | A | 10/1999 | Thenappan et al. | |
| 5,986,151 | A | 11/1999 | Van der Puy et al. | |
| 6,023,004 | A | 2/2000 | Thenappan et al. | |
| 6,025,532 | A | 2/2000 | Sage | |
| 6,031,141 | A | 2/2000 | Mallikarjuna et al. | |
| 6,041,620 | A * | 3/2000 | Olszewski et al. | 62/612 |
| 6,041,621 | A | 3/2000 | Olszewski et al. | |
| 6,045,444 | A | 4/2000 | Zima et al. | |
| 6,059,027 | A | 5/2000 | Lake et al. | |
| 6,076,372 | A | 6/2000 | Acharya | |
| 6,089,032 | A | 7/2000 | Tractenberg | |
| 6,111,150 | A | 8/2000 | Sakyu et al. | |
| 6,124,510 | A | 9/2000 | Elsheikh et al. | |
| 6,173,902 | B1 | 1/2001 | Bauer et al. | |
| 6,176,102 | B1 | 1/2001 | Praxair | |
| 6,235,951 | B1 | 5/2001 | Sakyu et al. | |
| 6,258,292 | B1 | 7/2001 | Turner et al. | |
| 6,274,799 | B1 | 8/2001 | Merkel et al. | |
| 6,300,378 | B1 | 10/2001 | Tapscott | |
| 6,304,803 | B1 | 10/2001 | Dao | |
| 6,316,681 | B1 | 11/2001 | Yoshikawa et al. | |
| 6,327,866 | B1 | 12/2001 | Novak et al. | |
| 6,369,284 | B1 | 4/2002 | Nappa et al. | |
| 6,374,629 | B1 | 4/2002 | Oberle | |
| 6,382,305 | B1 | 5/2002 | Sano | |
| 6,516,837 | B2 | 2/2003 | Thomas et al. | |
| 6,530,421 | B1 | 3/2003 | Filius et al. | |
| 6,548,719 | B1 | 4/2003 | Nair et al. | |
| 6,589,355 | B1 | 7/2003 | Thomas et al. | |
| 1,069,427 | A1 | 10/2003 | Singh et al. | |
| 1,069,521 | A1 | 10/2003 | Thomas et al. | |
| 6,640,841 | B2 | 11/2003 | Thomas | |
| 6,695,973 | B1 | 2/2004 | Musso | |
| 1,082,607 | A1 | 4/2004 | Singh et al. | |
| 1,082,659 | A1 | 4/2004 | Singh et al. | |
| 1,082,681 | A1 | 4/2004 | Singh et al. | |
| 1,083,752 | A1 | 4/2004 | Singh et al. | |
| 6,783,691 | B1 | 8/2004 | Bivens | |
| 6,809,226 | B1 | 10/2004 | Pennetreau et al. | |
| 6,843,930 | B2 | 1/2005 | Cho | |
| 6,858,571 | B2 | 2/2005 | Pham et al. | |
| 6,958,424 | B1 | 10/2005 | Nair et al. | |
| 6,972,271 | B2 | 12/2005 | Thomas et al. | |
| 6,991,532 | B2 | 1/2006 | Goldsmith | |
| 6,991,744 | B2 | 1/2006 | Mahler | |
| 7,105,152 | B1 | 9/2006 | Schultz | |
| 7,230,146 | B2 | 6/2007 | Merkel et al. | |
| 7,279,451 | B2 | 10/2007 | Singh et al. | |
| 7,345,209 | B2 | 3/2008 | Mukhopadhyay et al. | |
| 7,524,805 | B2 | 4/2009 | Singh et al. | |
| 2003/0127115 | A1 | 7/2003 | Thomas et al. | |
| 2004/0119047 | A1 | 6/2004 | Singh et al. | |
| 2004/0127383 | A1 | 7/2004 | Pham et al. | |
| 2004/0256594 | A1 | 12/2004 | Singh et al. | |
| 2005/0020862 | A1 | 1/2005 | Tung et al. | |
| 2005/0054741 | A1 | 3/2005 | Zipfel et al. | |
| 2005/0090698 | A1 | 4/2005 | Merkel et al. | |
| 2005/0107246 | A1 | 5/2005 | Thomas et al. | |
| 2005/0171391 | A1 | 8/2005 | Janssens et al. | |
| 2005/0241805 | A1* | 11/2005 | Singh et al. | 165/104.12 |
| 2006/0010872 | A1* | 1/2006 | Singh et al. | 60/671 |
| 2006/0243944 | A1 | 11/2006 | Minor et al. | |
| 2007/0098646 | A1 | 5/2007 | Nappa et al. | |
| 2007/0100010 | A1 | 5/2007 | Creazzo et al. | |
| 2007/0108403 | A1 | 5/2007 | Sievert et al. | |
| 2007/0284555 | A1 | 12/2007 | Leck et al. | |
| 2008/0098755 | A1* | 5/2008 | Singh et al. | 62/119 |
| 2008/0099190 | A1* | 5/2008 | Singh et al. | 165/104.21 |
| 2009/0272134 | A1* | 11/2009 | Hulse et al. | 62/112 |

FOREIGN PATENT DOCUMENTS

| | | |
|---|---|---|
| EP | 0522639 | 1/1993 |
| EP | 0644173 | 5/1993 |
| EP | 0 681 933 A1 | 11/1995 |
| EP | 0974571 | 1/2000 |
| EP | 1055439 | 11/2000 |
| EP | 1191080 | 7/2002 |
| EP | 0971571 | 4/2003 |
| GB | 950 876 | 2/1964 |
| JP | 63-211245 | 9/1988 |
| JP | 63-303950 | 12/1988 |
| JP | 04-110388 A | 4/1992 |
| JP | 04110388 * | 4/1992 |
| JP | 8-157847 A | 6/1996 |
| JP | 10007604 | 10/1998 |
| JP | 11140002 | 5/1999 |
| JP | 2000169404 | 6/2000 |
| RU | 2073058 C1 | 12/1994 |
| WO | 1995/04021 | 2/1995 |
| WO | 1996/01797 | 1/1996 |
| WO | 1998/33755 | 8/1998 |
| WO | WO 03064508 | 8/2003 |
| WO | 2004/37752 A2 | 5/2004 |
| WO | 2004/037913 | 5/2004 |
| WO | WO2004/037752 | 5/2004 |
| WO | 2005/012212 | 2/2005 |
| WO | 2005/42451 | 5/2005 |
| WO | 2005/042663 | 5/2005 |
| WO | 2005/103187 | 11/2005 |
| WO | 2005/103188 | 11/2005 |
| WO | 2005/103190 | 11/2005 |
| WO | 2005/103191 | 11/2005 |
| WO | 2005/103192 | 11/2005 |
| WO | 2005/0105947 | 11/2005 |
| WO | 2007/002625 | 1/2007 |

OTHER PUBLICATIONS

Request for Inter Partes Reexamination of U.S. Patent No. 7,524,805, "Azeotropic-Like Compositions of Tetrafluoropropene and Hydrofluorocarbons," Reexamiantion Control No. 95/000,574. US.

Request for Inter Partes Reexamination of U.S. Patent No. 7,279,451, "Compositions Containing Fluorine Substituted Olefins," Reexamination Control No. 95/000,576. US.

Billy C. Langley, "Automotive Air Conditioning," *Refrigeration and Air Conditioning*, 3d Ed. Prentice-Hall, (1986) pp. 525-526 US.

Althouse, et al., "Heat Pump Systems, Principles, Applications," *Modern Refrigeration and Air Conditioning*, Chapter 26, pp. 999, 1002-1003. The Goodheart-Wilcox Co., Inc. (1968) US.

Meyer Kutz (Editor), "Refrigerants," *Mechanical Engineers' Handbook*, 2d Ed., p. 1887, John Wiley & Sons, Inc. (publ.) (1998) US.

Althouse et al., "Automobile Air Conditioning," *Modern Refrigeration and Air Conditioning*, Chapter 27,, pp. 949-976. The Goodheart-Wilcox Co., Inc. (1998) US.

H. Michael Hughes, "Refrigerants," *Refrigeration Systems for HVAC*, Section 6, pp. 6.1.2-6.1.15, McGraw-Hill Co. (1997) US.

Society of Heating, Air-Conditioning and Sanitary Engineers, "Chapter 1. Refrigeration System and Heat Pump Overview," *Air Conditioning and Sanitary Engineering Handbook*, 12$^{th}$ Ed. (Mar. 25, 1995) JP.

Sybil Parker (Ed.), *McGraw-Hill Encyclopedia of Engineering*, 2d Ed. (1993), p. 525 (Heat Pump). US.

M Spatz et al., "HF0-1234yf Low GWP Refrigerant," Presentation given at *SAE 2008 Alternate Refrigerant Systems Symposium*, Scottsdale (AZ), Jun. 10-12, 2008. US.

M Spatz et al., "HFO-1234yf Low GWP Refrigerant," Presentation given at International Refrigeration and Air Conditioning Conference at Purdue, Jul. 14-17, 2008 US.

LJM Kuipers, "Impact of the decrease in CFC Emissions on refrigeration: target of the IIR initiative," *Int. J. Refrigeration*, pp. 35-51, vol. 11, No. 6. (1988) US.

Directive 2006/40/EC of the European Parliament and of the Council of May 17, 2006 relating to emissions from air-conditioning systems in motor vehicles and amending Council Directive 70/156/EC. EU. European Parliament Session Document. "Report On The Proposal For A European Parliament And Council Regulation On Certain Fluorinated Greenhouse Gases." (COM(2003)492-C5-0397/Mar. 2003/0189(COD)), Mar. 18, 2004.

J Jones, CJ Morrissey, Nearly Azeotropic mixtures to replacere frigerant 12, *NASA Tech Brief*, vol. 16, No. 8, Item #122 from JPL New Technology Report NPO 18030//528, pp. 1-39, Aug. 1992 US.

"Compatibility With Refrigeration Oil," Extract from the *Daikin Handbook*, Jun. 2001, pp. 25-28.
Sjoholm et al., "Twin-Screw Compressor Performance and Suitable Lubricants With HFC-134a," International Compressor Engineering Conference at Purdue (Jul. 17-20, 1990), Proceedings vol. II, pp. 733-40. US.
Honeywell's submission to EPO dated May 2, 2009 together with documents cited and referred to therein. EP (documents submitted herein are below (16a-16k).
Althouse et al., "Basic Air Conditioning Systems," *Modern Refrigeration and Air Conditioning*, Chapter 19, pp. 679-705. The Goodheart-Wilcox Co., Inc. (pub.) (1988) US.
Billy C. Langley, "Automotive Air Conditioning," *Refrigeration and Air Conditioning*, 3d Ed. Prentice-Hall, (1986) Chapter 21, pp. 525-553.
European Parliament, "Report on the proposal for a European Parliament and Council regulation on certain fluorinated greenhouse gases," (Com(2003)492-C5-0397/03-2003/0189(COD)) Mar. 18, 2004 (EP).
Pollution Prevention Fact Sheet No. 10, Pollution Prevention Program. Federal Programs Division, Managing Controlled Refrigerants, Jan. 1997, pp. 1-8 CA.
Graham, "Global Market for Heating, Ventilation and Air-Conditioning Systems," About Automotive—Research Report, 2006 Edition. GB.
Ignatio De Alvaro et al., "Market Report, Minisplits," BSRIA Report No. 18588/5, May 2004.
Emil Milker et al., "Worldwide Air Conditioning," BSRIA Report No. 19947B, BSRIA Limited, Mar. 2008, GB.
National Technical Information Service, U.S. Dept. Of Commerce, Support: Letter from DuPont Haskell Lab to USEPA Regarding Results of Bacterial Reverse Mutation Assay Conducted With 1-Propene, 1,1,3,3,3-Pentafluoro-. Apr. 17, 2000.
Morrissey, C.J., "Nearly Azeotropic Mixtures to Replace Refrigerant 12," From National Aeronautics and Space Administration Contract No. Nas 7-918, Aug. 1992, NASA Tech Brief, vol. 16, No. 8, Item #122. US.
1234yf OEM Group, "Update: 1234yf as a replacement for R134a," published following MAC (Mobile Air-Conditioning) Summit in 2008, see pp. 14, 15 and 18.
PRNewswire, Honeywell's Low-Global-Warming-Potential Refrigerant Endorsed by SAE International Cooperative Research Project, internet article, www.prnewswire.co.uk/cgi/news/release?id=244472 (Dec. 8, 2008) GB.
Takahashi, "Alternative Technologies for Refrigeration And Air-Conditioning Applications," *Environmental Chemistry of Chlorofluorocarbon and Control Engineering*, (Quarterly Issue of General Review of Chemistry, 1991, No. 11) JP.
Kenji Tojo, "Insulations Systems and Materials for Hermetic Motor, " *Latest new refrigerant and insulation system technology*, Chapter 7, First Edition, (1996) JP.
Honeywell International Inc. Response to Notice of Opposition of Arkema France and exhibits cited therein.
Althouse et al., "Basic Air Conditioning Systems," *Modern Refrigeration and Air Conditioning*, Chapter 19, pp. 679-705. The Goodheart-Wilcox Co., Inc. (pub.) (1988) US (previously cited).
Graham, "Global Market for Heating, Ventilation and Air-Conditioning Systems," About Automotive—Research Report, 2006 Edition. GB (previously cited).
Ignatio De Alvaro et al., "Market Report, Minisplits," BSRIA Report No. 18588/5, May 2004. (previously cited).
Milker, et al., "Report, Worldwide Air Conditioning," BSRIA, Report No. 19947B, Mar. 2008. GB.
Pollution Prevention Fact Sheet No. 10, Pollution Prevention Program. Federal Programs Division, Managing Controlled Refrigerants, Jan. 1997, pp. 1-8 CA (previously cited).
About MACS Worldwide, "Welcome to the Mobile Air Conditioning Society (MACS) Worldwide", webpage printout http://www.macsw.org//AM/Template.cfm?Section-Home.
Billy C. Langley, "Automotive Air Conditioning," *Refrigeration and Air Conditioning*,3d Ed. Prentice-Hall, (1986) Chapter 21, pp. 525-553 US (previously cited).
U.S. Patent No. 3,607,755 (Murphy et al.) Sep. 21, 1975.

H. Kruse, "CFC Research Programmes in Western Europe," Int. J. Refrig. 1990, vol. 13 (Presented at the 1989 ASHRAE CFC Technology Conference, Gaithersburg, MD (Sep. 27-28, 1989). US.
Bivens et al., "Fluoroethers and Other Next-Generation Fluids," ASHRAE/NIST Refrigerants Conference —Oct. 1997.
Smith, New Chemical Alternatives for CFCs and HCFCs, U.S. Environmental Protection Agency, EPA-600/F-92-012 (Mar. 24, 1992) US.
J. Calm and D. Didion et al., "Trade-Offs in Refrigerant Selections: Past, Present, and Future," ASHRAE/NIST Refrigerant Conference—Oct. 1977.
Denis Clodic, "Automobile Air Conditioning: Environmental Issues and Future Technical Alternatives," The globalization of automobile air conditioning. General review of refrigeration and air conditioning, May 2008 (translation).
R. Gicquel, "Thermodynamic Diagrams—Mixtures Used in Refrigeration." FR.
Weiss et al., "Current and Projected use of Refrigerants in Europe," ASHRAE/NIST Refrigerants Conference—Oct. 1997.
2006 Standard for Sepcifications for Fluorocarbon Refrigerants, Standard 700-Ari (Air-Conditioning & Refrigerant Institute), copyright 2006.
J Jones, CJ Morrissey, Nearly Azeotropic mixtures to replace refrigerant 12, *NASA Tech Brief*, vol. 16, No. 8, Item #122 from JPL New Technology Report NPO 18030//528, pp. 1-39, Aug. 1992 US (previously cited).
Kopko, "Beyond CFCs: Extending the Search for New Refrigerants," Supplied by The British Library.
1234yf OEM Group, "Update: 1234yf as a replacement for R134a," published following MAC (Mobile Air-Conditioning) Summit in 2008, see pp. 14, 15 and 18. (previously cited).
PRNewswire, Honeywell's Low-Global-Warming-Potential Refrigerant Endorsed by SAE International Cooperative Research Project, internet article, www.prnewswire.co.uk/cgi/news/release?id=244472 (Dec. 8, 2008) GB (previously cited).
Clodic, Automobile Air Conditioning: Environmental Issues and Future Technical Alternatives, The New Refrigerant Fluids. (translation) (May 2008) FR.
"Arkema Beefs Up Chemicals; Eyes Acquisition of Acrylics Assets," Business & Finance News, Chemical Week, Nov. 17, 2008, p. 19.
Executed Assignment of Inventorship for U.S. Application, Honeywell Reference H0003965CIP. US.
Exeduted Declaration of Inventorship for U.S. Appl. No. 10/837,525, Honeywell Reference H0003965CIP. US.
U.S. Patent No. 7,279,451 (previously cited) Apr. 29, 2004.
National Technical Information Service, U.S. Dept. Of Commerce, Support: Letter from DuPont Haskell Lab to USEPA Regarding Results of Bacterial Reverse Mutation Assay Conducted With 1-Propene, 1,1,3,3,3-Pentafluoro-. Apr. 17, 2000 (previously cited).
Althouse et al., "Automobile Air Conditioning," *Modern Refrigeration and Air Conditioning*, Chapter 27,, pp. 949-976. The Goodheart-Wilcox Co., Inc. (1998) US (previously cited).
Honeywell webpage printout, re: Honeywell Genetron Refrigerants, "Commercial AC Products," (Jul. 14 2010) US.
Honeywell webpage printout, re: Honeywell Genetron Refrigerants, "Mobile A.C," (Jul. 14, 2010) US.
Honeywell webpage printout, re: Honeywell Genetron Refrigerants, "Genetron 134a," (Jul. 14, 2010) US.
OJ Nielsen et al., "Atmospheric chemistry of $CF_3 CF=CH_2$ : Kinetics and mechanisms of gas-phase reactions with Cl atoms, OH radicals, and $O_3$ " *Science Direct*,Chemical Physics Letters 439 (2007) pp. 18-22 (www.sciencedirect.com) US.
ANSI/ASHRAE Standard 34-2007 Designation and Safety Classification of Refrigerants, 2007.
BSR/ASHRAE Addendum z zu ANSI-ASHRAE Standard 34-2007, Public Review Draft, Sep. 2008.
M Spatz et al., "HFO-1234yf Low GWP Refrigerant," Presentation given at SAE 2008 Alternate Refrigerant Systems Symposium, Scottsdale (AZ), (Jun. 10-12, 2008) U.S.
V.I. Orkin et al., Rate Constants for the Reactions of OH with HFC-245cb ($CH_3Cl$ Fluoroalkenes ($CH_2CHCF_3$, $CH_2CFCF_3$, $CF_2CFCF_3$ and $CF_2CF_2$, *J.Phys Chem. A*, vol. 101. pp. 9118-9124 (1997) US.

Wikipedia (the free encyclopedia) entry of Jul. 14, 2010, "HVAC, Background, Heating, Ventilating, Air conditioning, Energy Efficiency, HVAC Industry and Standards," http://en.wikipedia.orq/wiki/HVAC; and collection of patent applications disclosing HVAC systems in automobiles.
Proposal for the Regulation of the European Parliament and of the Council on certain fluorinated greenhouse gases—Aug. 11, 2003.
Orkin et al., "Photochemistry of Bromine—containing Fluorinated Akenes; Reactivity toward OH and UV Spectra," J. Phys. Chem. A 2002, vol. 106, pp. 10195-10199 US.
Calorix Heat Pumps Ltd., "Energy Efficient Hot Water Heating," booklet, 4 pages. US.
Mitsubishi Electric, "Water Heating Units," (leaflet), (4 pages) GB.
IVT Heat Pumps, "Greenline," (leaflet), (2 pages) SE.
Conergy, "Conergy Heat Pump; The Clever Choice for Hot Water," (leaflet), (2 pages) AU.
Dimplex, "Hot water heat pump with sheet steel casing, air duct connection and additional heat exchanger," Data Sheet (1 page) DE.
Honeywell International Inc., "Guide to Alternative Refrigerants," (leaflet), (2 pages) US.
M Tekeuchi et al., "An Environmentally Friendly, Highly Efficient, Lightweight Scroll Compressor (QS90) For Car Air Conditioners" *Mitsubishi Heavy Industries, Ltd. Technical.Review*, vol. 45, No. 3, pp. 24-26 (Sep. 2008) US.
New Refrigerant Insulating System Technology, pp. 75-78 (Apr. 15, 1996).
The Properties of Gases and Liquids, Poling et al, 2001, excerpts from chapters 2, 3, 4, 6 and 7.
Discussion on Modelling of Properties.
Fundamental Equation of State for 2,3,3,3-Tetrafluoropropene (HFO-1234yf) Ryo Akasaka et al. (HFO-1234yf Property Sheet).
Opposition 1—Arkema France (translation).
Opposition 1—Arkema further opposition documents (translation).
Opposition 2—Daikin Industris Ltd (translation).
Opposition 3—Asahi Glass Company Ltd.
Opposition 4—Daimler AG.
Opposition 5—ACEA European Automobile Manufactures Association.
Opposition 6—Anonymous.
Opposition 7—Bayerische Motoren Werke AG (translation).
Opposition 8—Mexichem Amanco Holdings SA.
Opposition 9—Solvay Fluor GmbH.
Observation 10—Potter Clarkson LLP, Third Party Observations to EP Patent Appl. No. 05744161.0, filed by Inneos Fluor Limited, Feb. 26, 2009. EP.
Observation 11—Anonymous—Filed by Arnason/Faktor, Intellectual Property Consulting, Reykjavik, Iceland, Dec. 9, 2008. IE.
Observation 12—Anonymous—Filed by Dr. Modiano & Associates, Milano, Feb. 26, 2009. IT.
Observation 13—Anonymous—Anonymous—Filed by Dr. Modiano & Associates, Milano, Apr. 2, 2009. IT.
English Translation of Official Action in Connection With Corresponding Japanese Patent Application No. 2004- 547148.
Response to Japanese office action (not translated) and English language translation of claims as amended.
English Translation of JP Anonymous Submission of Prior Art References to Opposition to JP Application No. 2004-547148, dated Jun. 8, 2010.
Notice of Allowance is JP Application No. 2004-547148 (not translated) and allowed claims.
Reexamination Request—451 Patent.
Reexamination Request—805 Patent.
Additional Non-PAtent Literature Documents Cited in U.S. Appl. No. 10/694,273.
Saunders and Frisch, "Polyurethanes Chemistry & Technology," vol. XVI, Part I and Part II Technology, John Wiley and Sons, New York, NY (1962), pp. 193-201 and 219-223. US.
Downing, Ralph C., "Fluorocarbon Refrigerants Handbook," Prentice Hall, Excepts from Chapter 3 and Chapter 16. US.
Additional Non-Patent Literature Documents Cited in U.S. Appl. 10/837,525 or 11/847,192.
Haszeldine, R. N. et al., "Free-radical Additions to Unsaturated Systems. Part XVII. Reaction of Trifluoroiodomethane with Mixtures of Ethylene and Vinyl Fluoride and of Ethylene and Propene," J. Chem. Soc., Section C, Organic (3), pp. 414-421 (1970), XP002343900.
Henne et al., "Fluorinated Derivatives of Propane and Propylene VI," J. Am. Chern. Soc., 68, pp. 496-497 (1946).
Kimura, et al., "Poly(ethylene glycols) and poly(ethylene glycol)-grafted copolymers are extraordinary catalysts for dehydrohalogenation under two-phase and three-phase conditions," J. Org. Chern., 48,195-0198 (1983).
Knunyants I. L. et al., "Reactions of Fluoro Olefins Communication 13, Catalytic DJ Hydrogenation of Perfluoro Oletins," Bulletin of the Academy of Sciences of the USSR, pp. 1312-1317 XPOO0578879.
Tarrant, et al., "Free Radical Additions Involving Fluorine Compounds. IV. The Addition of Dibromodifluoromethane to Some Fluoro06 1etins," J. Am. Chern Soc., 77,2783-2786 (1955).
Kunshenko, B. V. et al., "Reaction of Organic Compounds with SF4-HF-Halogenating System VII. Reactions of Oletins with the SF4-HF-Cl2(Br2) System," Odessa DM Polytechnicallnstitute, Institute of Organic Chemistry, Academy of Sciences of the Ukraine, Kiev., Translated from Zhuranl Organicheskoi Khimii, 28(4), 672-80 (1982), Original article submitted Aug. 24,1989. XP002344564.
Additional Non-Patent Literature Documents Cited in U.S. Appl. No. 11/475,605 and Divisionals Thereof.
Database WPI Section Ch, Week 199221 Derwent Publications Ltd., London, GB; Class E16, AN 1992-172539 XP002344657.
Additional Non-Patent Literature Documents Cited in U.S. Appl. No. 10/837,526; 11/119,053; 12/198,411.
Written Opinion of International Search Authority for PCT/US2005/14847.
Albert W. Noyes, Editor, The Journal of the American Chemical Society, vol. LXXVII; Apr.-Jun. 1955 pp. 3149-3151. US.
Additional Non-Patent Literature Documents Cited in U.S. Appl. No. 11/474,887 and Divisional and Continuations Thereof.
Jan H. Schutt, "Polyurethane Foam Industry Prepares for 'Zero ODP-',"Plastics Technology—Internet article (http://vvww.plasticstechnology.com/articles/199911fa3.html).
Perry Romanowski, "Polyurethane, How Plastics Are Made," Gale Edit, Volumes-Polyurethane. US.
Additional Non-Patent Literature Documents Cited in Parent U.S. Appl. No. 10/695,212 and 11/385,259.
International Search Report for PCT/US04/35132 (corresponding 11/385,259).
EPO Communication in EP Application No. 08011766.6, Filed: Oct. 25, 2004, Applicant: Honeywell International Inc., Re: Third Party Observations filed Feb. 18, 2011 by Potter Clarkson LLP on behalf of anonymous third party. (EP).
Patent Owner's Response to the First Office Action Mailed Dec. 22, 2010, filed Mar. 21, 2011. (in In re Reexamination Control U.S. Appl. No. 95/000,576, Filed Oct. 5, 2010 for U.S. Patent No. 7,279,451).
Declaration of Rajiv R. Singh filed Mar. 21, 2011. (in In re Reexamination Control U.S. Appl. No. 95/000,576, Filed Oct. 5, 2010 for U.S. Patent No. 7,279,451).
Exhibit A—Rajiv Ratna Singh—U.S. Patents, (as attached to Declaration to Rajiv Ratna Singh, filed Mar. 21, 2011 in Patent Owner's Response to the First Office Action dated Dec. 22, 2010 in In re Reexamination Control U.S. Appl. No. 95/000,576, Filed Oct. 5, 2010 for U.S. Patent No. 7,279,451.).
Exhibit B—Rule 132 Declaration of George Rusch, dated Oct. 15, 2007 and Rule 132 Declaration of George Rusch date Apr. 25, 2007 (as attached to Declaration of Rajiv Ratna Singh, filed Mar. 21, 2011 in Patent Owner's Response to the First Office Action date Dec. 22, 2010 in In re Reexamination Control U.S. Appl. No. 95/000,576, Filed Oct. 5, 2010 for U.S. Patent. No. 7,279,451.).
Exhibit C—European Centre For Ecotoxicology and Toxicology of Chemicals (ECETOC), "Toxcity of Possible Impurities and By-products in Fluorocarbon Products," Technical Report No. 103, (pp. 1 to 186), ISSN-0733-8072-103, Dec. 2008, Brussels, BE. (as attached to Declaration of Rajiv Ratna Singh, filed Mar. 21, 2011 in Patent Owner's Response to the First Office Action dated Dec. 22, 2010 in In re Reexamination Control U.S. Appl. No. 95/00,576, Filed Oct. 5, 2010 for U.S. Patent No. 7,279,451.).
Exhibit D—Translation of JP Patent Application H4-110388, published Apr. 10, 1992 ("Inagaki") (as attached to Declaration of Rajiv Ratna Singh, filed Mar. 21, 2011 in Patent Owner's Response to the First Office Action dated Dec. 22, 2010 in In re Reexamination Control U.S. Appl. No. 95/000,576, Filed Oct. 5, 2010 for U.S. Patent No. 7,279,451.).

Exhibit E—Denis Clodic, "Automobile Air-Conditioning: Environmental Stakes and Future Technical Options," Journal of Cold and Air-conditioning, May 2008, original and certified translation, pp 47-52. FR (as attached to Declaration of Rajiv Ratna Singh, filed Mar. 21, 2011 in Patent Owner's Response to the First Office Action dated Dec. 22, 2010 in In re Reexamination Control U.S. Appl. No. 95/000,576, Filed Oct. 5, 2010 for U.S. Patent No. 7,279,451.).

Exhibit F—Natasha Alperowicz, "Arkema Beefs Up Chemicals; Eyes Acquisition of Acrylics Assets," Chemical Week, Nov. 17, 2008, p. 19. (as attached to Declaration of Rajiv Ratna Singh, filed Mar. 21, 2011 in Patent Owner's Response to the First Office Action dated Dec. 22, 2010 in In re Reexamination Control U.S. Appl. No. 95/000,576, Filed Oct. 5, 2010 for U.S. Patent No. 7,279,451.).

Exhibit G—Industry Presentation, MAC Sumit 2008, 1234yf OEM Group, "Update: 1234yf as a replacement for R134a," pp. 1-20). (as attached to Declaration of Rajiv Ratna Singh, filed Mar. 21, 2011 in Patent Owner's Response to the First Office Action dated Dec. 22, 2010 in In re Reexamination Control U.S. Appl. No. 95/000,576, Filed Oct. 5, 2010 for U.S. Patent No. 7,279,451.).

Exhibit H—Paul Weissler, Ed., "EPA presses for fast switch to A/C refrigerant R-1234yf," Automotive Engineering International Online, Apr. 7, 2009, http://www.sae.org/mags/aei/6137. (as attached to Declaration of Rajiv Ratna Singh, filed Mar. 21, 2011 in Patent Owner's Response to the First Office Action dated Dec. 22, 2010 in In re Reexamination Control U.S. Appl. No. 95/000,576, Filed Oct. 5, 2010 for U.S. Patent 7,279,451.).

Exhibit I—"GM First to Market Greenhouse Gas-Friendly Air Conditioning Refrigerant in U.S.," Jul. 23, 2010, online article at www.gm.com/corporate/responsibility/environment/news/2010/air_conditioning_refrigerant. US (as attached to Declaration of Rajiv Ratna Singh, filed Mar. 21, 2011 in Patent Owner's Response to the First Office Action dated Dec. 22, 2010 in In re Reexamination Control U.S. Appl. No. 95/000,576, Filed Oct. 5, 2010 for U.S. Patent No. 7,279,451.).

Exhibit J—Réne Müller, "First-Class Air Conditioning," AutomobilKONSTRUKTION, Feb. 2009, (as attached to Declaration of Rajiv Ratna Singh, filed Mar. 21, 2011 in Patent Owner's Response to the First Office Action dated Dec. 22, 2010 in In re Reexamination Control U.S. Appl. No. 95/000,576, Filed Oct. 5, 2010 for U.S. Patent No. 7,279,451.).

Exhibit K—"SAE Endorses Honeywell Refrigerant," Refrigeration and Air Conditioning Magazine (RAC). Jan. 2009. (as attached to Declaration of Rajiv Ratna Singh, filed Mar. 21, 2011 in Patent Owner's Response to the First Office Action dated Dec. 22, 2010 in In re Reexamination Control U.S. Appl. No. 95/000,576, Filed Oct. 5, 2010 for U.S. Patent No. 7,279,451.).

Exhibit L—"EPA Approves New Coolant for Car Air Conditioning Systems/Better climate protection without harming the ozone layer," EPA: United States Environmental Protection Agency, Release date: Feb. 28, 2011. (as attached to Declaration of Rajiv Ratna Singh, filed Mar. 21, 2011 in Patent Owner's Response to the First Office Action dated Dec. 22, 2010 in In re Reeamination Control U.S. Appl. No. 95/000, 576, Filed Oct. 5, 2010 for U.S. Patent No. 7,279,451.).

* cited by examiner

US 8,033,120 B2

COMPOSITIONS AND METHODS CONTAINING FLUORINE SUBSTITUTED OLEFINS

RELATED APPLICATIONS

The present application is a Divisional of and claims the priority benefit of U.S. patent application Ser. No. 10/694,273, filed Oct. 27, 2003 (now U.S. Pat. No. 7,534,366 issued May 19 2009), which is incorporated herein by reference and which in turn claims the benefit of Provisional Patent Application Nos. 60/421,263, and 60/421,435, each of which was filed on Oct. 25, 2002, and each of which is incorporated herein by reference. The present application is also a continuation-in-part and incorporates by reference each of the following United States Patent Applications: entitled "Fluorinated Alkene Refrigerant Composition," by Raymond Thomas, U.S. patent application Ser. No. 10/695,212, filed Oct. 27, 2003, now abandoned in favor of U.S. patent application Ser. No. 11/385,259, filed Mar. 20, 2006, now pending, and entitled "Process For Producing Fluoropropenes," by Hsueh Sung Tung et al, U.S. patent application Ser. No. 10/694,272, filed Oct. 27, 2003, (now U.S. Pat. No. 7,230,146 issued Jun. 12, 2007).

FIELD OF THE INVENTION

This invention relates to compositions having utility in numerous applications, including particularly refrigeration systems, and to methods and systems which utilize such compositions. In preferred aspects, the present invention is directed to refrigerant compositions which comprise at least one multi-fluorinated olefin of the present invention.

BACKGROUND OF THE INVENTION

Fluorocarbon based fluids have found widespread use in many commercial and industrial applications. For example, fluorocarbon based fluids are frequently used as a working fluid in systems such as air conditioning, heat pump and refrigeration applications. The vapor compression cycle is one of the most commonly used type methods to accomplish cooling or heating in a refrigeration system. The vapor compression cycle usually involves the phase change of the refrigerant from the liquid to the vapor phase through heat absorption at a relatively low pressure and then from the vapor to the liquid phase through heat removal at a relatively low pressure and temperature, compressing the vapor to a relatively elevated pressure, condensing the vapor to the liquid phase through heat removal at this relatively elevated pressure and temperature, and then reducing the pressure to start the cycle over again.

While the primary purpose of refrigeration is to remove heat from an object or other fluid at a relatively low temperature, the primary purpose of a heat pump is to add heat at a higher temperature relative to the environment.

Certain fluorocarbons have been a preferred component in many heat exchange fluids, such as refrigerants, for many years in many applications. For, example, fluoroalkanes, such as chlorofluoromethane and chlorofluoroethane derivatives, have gained widespread use as refrigerants in applications including air conditioning and heat pump applications owing to their unique combination of chemical and physical properties. Many of the refrigerants commonly utilized in vapor compression systems are either single components fluids or azeotropic mixtures.

Concern has increased in recent years about potential damage to the earth's atmosphere and climate, and certain chlorine-based compounds have been identified as particularly problematic in this regard. The use of chlorine-containing compositions (such as chlorofluorocarbons (CFC's), hydrochlorofluorocarbons (HCF's) and the like) as refrigerants in air-conditioning and refrigeration systems has become disfavored because of the ozone-depleting properties associated with many of such compounds. There has thus been an increasing need for new fluorocarbon and hydrofluorocarbon compounds and compositions that offer alternatives for refrigeration and heat pump applications. For example, it has become desirable to retrofit chlorine-containing refrigeration systems by replacing chlorine-containing refrigerants with non-chlorine-containing refrigerant compounds that will not deplete the ozone layer, such as hydrofluorocarbons (HFC's).

It is generally considered important, however, that any potential substitute refrigerant must also possess those properties present in many of the most widely used fluids, such as excellent heat transfer properties, chemical stability, low- or no-toxicity, non-flammability and lubricant compatibility, among others.

Applicants have come to appreciate that lubricant compatibility is of particular importance in many of applications. More particularly, it is highly desirably for refrigeration fluids to be compatible with the lubricant utilized in the compressor unit, used in most refrigeration systems. Unfortunately, many non-chlorine-containing refrigeration fluids, including HFC's, are relatively insoluble and/or immiscible in the types of lubricants used traditionally with CFC's and HFC's, including, for example, mineral oils, alkylbenzenes or poly (alpha-olefins). In order for a refrigeration fluid-lubricant combination to work at a desirable level of efficiently within a compression refrigeration, air-conditioning and/or heat pump system, the lubricant should be sufficiently soluble in the refrigeration liquid over a wide range of operating temperatures. Such solubility lowers the viscosity of the lubricant and allows it to flow more easily throughout the system. In the absence of such solubility, lubricants tend to become lodged in the coils of the evaporator of the refrigeration, air-conditioning or heat pump system, as well as other parts of the system, and thus reduce the system efficiency.

With regard to efficiency in use, it is important to note that a loss in refrigerant thermodynamic performance or energy efficiency may have secondary environmental impacts through increased fossil fuel usage arising from an increased demand for electrical energy.

Furthermore, it is generally considered desirably for CFC refrigerant substitutes to be effective without major engineering changes to conventional vapor compression technology currently used with CFC refrigerants.

Flammability is another important property for many applications. That is, it is considered either important or essential in many applications, including particularly in heat transfer applications, to use compositions which are non-flammable. Thus, it is frequently beneficial to use in such compositions compounds which are nonflammable. As used herein, the term "nonflammable" refers to compounds or compositions which are determined to be nonflammable as determined in accordance with ASTM standard E-681, dated 2002, which is incorporated herein by reference. Unfortunately, many HFC's which might otherwise be desirable for used in refrigerant compositions are not nonflammable. For example, the fluoroalkane difluoroethane (HFC-152a) and the fluoroalkene 1,1,1-trifluorpropene (HFO-1243zf) are each flammable and therefore not viable for use in many applications.

Higher fluoroalkenes, that is fluorine-substituted alkenes having at least five carbon atoms, have been suggested for use as refrigerants. U.S. Pat. No. 4,788,352—Smutny is directed to production of fluorinated $C_5$ to $C_8$ compounds having at least some degree of unsaturation. The Smutny patent identifies such higher olefins as being known to have utility as refrigerants, pesticides, dielectric fluids, heat transfer fluids, solvents, and intermediates in various chemical reactions. (See column 1, lines 11-22).

While the fluorinated olefins described in Smutny may have some level of effectiveness in heat transfer applications, it is believed that such compounds may also have certain disadvantages. For example, some of these compounds may tend to attack substrates, particularly general-purpose plastics such as acrylic resins and ABS resins. Furthermore, the higher olefinic compounds described in Smutny may also be undesirable in certain applications because of the potential level of toxicity of such compounds which may arise as a result of pesticide activity noted in Smutny. Also, such compounds may have a boiling point which is too high to make them useful as a refrigerant in certain applications.

Bromofluoromethane and bromochlorofluoromethane derivatives, particularly bromotrifluoromethane (Halon 1301) and bromochlorodifluoromethane (Halon 1211) have gained widespread use as fire extinguishing agents in enclosed areas such as airplane cabins and computer rooms. However, the use of various halons is being phased out due to their high ozone depletion. Moreover, as halons are frequently used in areas where humans are present, suitable replacements must also be safe to humans at concentrations necessary to suppress or extinguish fire.

Applicants have thus come to appreciate a need for compositions, and particularly heat transfer compositions, fire extinguishing/suppression compositions, blowing agents, solvent compositions, and compatabilizing agents, that are potentially useful in numerous applications, including vapor compression heating and cooling systems and methods, while avoiding one or more of the disadvantages noted above.

SUMMARY

Applicants have found that the above-noted need, and other needs, can be satisfied by compositions comprising one or more C3 or C4 fluoroalkenes, preferably compounds having Formula I as follows:

$$XCF_zR_{3-z} \quad (I)$$

where X is a $C_2$ or a $C_3$ unsaturated, substituted or unsubstituted, alkyl radical, each R is independently Cl, F, Br, I or H, and z is 1 to 3.

The present invention provides also methods and systems which utilize the compositions of the present invention, including methods and systems for heat transfer, foam blowing, solvating, and aerosol generation.

DETAILED DESCRIPTION OF PREFERRED EMBODIMENTS

The Compositions

The present invention is directed to compositions comprising at least one fluoroalkene containing from 3 to 4 carbon atoms and at least one carbon-carbon double bond. The fluoroalkene compounds of the present invention are sometimes referred to herein for the purpose of convenience as hydrofluoro-olefins or "HFOs" if they contain at least one hydrogen. Although it is contemplated that the HFOs of the present invention may contain two carbon-carbon double bonds, such compounds at the present time are not considered to be preferred.

As mentioned above, the present compositions comprise one or compounds in accordance with Formula I. In preferred embodiments, the compositions include compounds of Formula II below:

(II)

where each R is independently Cl, F, Br, I or H
R' is $(CR_2)_nY$,
Y is $CRF_2$
and n is 0 or 1.

In highly preferred embodiments, Y is $CF_3$, n is 0 and at least one of the remaining Rs is F.

Applicants believe that, in general, the compounds of the above identified Formulas I and II are generally effective and exhibit utility in refrigerant compositions, blowing agent compositions, compatibilizers, and solvent compositions of the present invention. However, applicants have surprisingly and unexpectedly found that certain of the compounds having a structure in accordance with the formulas described above exhibit a highly desirable low level of toxicity compared to other of such compounds. As can be readily appreciated, this discovery is of potentially enormous advantage and benefit for the formulation of not only refrigerant compositions, but also any and all compositions which would otherwise contain relatively toxic compounds satisfying the formulas described above. More particularly, applicants believe that a relatively low toxicity level is associated with compounds of Formula II, preferably wherein Y is $CF_3$, wherein at least one R on the unsaturated terminal carbon is H, and at least one of the remaining Rs is F. Applicants believe also that all structural, geometric and stereoisomers of such compounds are effective and of beneficially low toxicity.

In highly preferred embodiments, especially embodiments which comprise the low toxicity compounds described above, n is zero. Thus, in certain preferred embodiments the compositions of the present invention comprise one or more compounds selected from the group consisting of tetrafluoropropenes (HFO-1234), pentafluoropropenes (HFO-1225) and combinations of these.

It is even more preferred that the compounds of the present invention are the tetrafluoropropene and pentafluoropropene compounds in which the unsaturated terminal carbon has not more than one F substituent, specifically: 1,3,3,3-tetrafluoropropene (HFO-1234ze); 2,3,3,3-tetrafluoropropene (HFO-1234yf); and 1,2,3,3,3-pentafluoropropene (HFO-1225ye), and any and all stereoisomers of each of these. Applicant has discovered that such compounds have a very low acute toxicity level, as measured by inhalation exposure to mice and rats. On the other hand, applicants have found that a relatively high degree of toxicity may be associated with certain compounds adaptable for use with the present compositions, namely, those compounds which have more than one F on the terminal unsaturated carbon, or which do not have at least one H on the terminal unsaturated carbon. For example, applicants have discovered that 1,1,3,3,3-pentafluoropropene (HFO-1225zc) exhibits an unacceptably high degree of toxicity, as measured by inhalation exposure to mice and rats.

The preferred compounds of the present invention, namely, HFO-1225 and HFO-1234 are known materials and are listed in Chemical Abstracts databases. HFO-1225 is commercially available, from example from Syntex Chemical Co. Furthermore, methods are described generally in the patent literature for producing fluoroalkenes. For example, the production of fluoropropenes such as $CF_3CH=CH_2$ by catalytic vapor phase fluorination of various saturated and unsaturated halogen-containing $C_3$ compounds is described in U.S. Pat. Nos. 2,889,379; 4,798,818 and 4,465,786, each of which is incorporated herein by reference. U.S. Pat. No. 5,532,419, which is also incorporated herein by reference, discloses a vapor phase catalytic process for the preparation of fluoroalkene using a chloro- or bromo-halofluorocarbon and HF. EP 974,571, also incorporated herein by reference, discloses the preparation of 1,1,1,3-tetrafluoropropene by contacting 1,1,1,3,3-pentafluoropropane (HFC-245fa) in the vapor phase with a chromium-based catalyst at elevated temperature, or in the liquid phase with an alcoholic solution of KOH, NaOH, $Ca(OH)_2$ or $Mg(OH)_2$. In addition, methods for producing compounds in accordance with the present invention are described generally in connection with concurrently filed United States patent application Ser. No. 10/694,272 entitled "Process for Producing Fluorpropenes", which is also incorporated herein by reference.

The present compositions are believed to possess properties that are advantageous for a number of important reasons. For example, applicants believe, based at least in part on mathematical modeling, that the fluoroolefins of the present invention will not have a substantial negative affect on atmospheric chemistry, being negligible contributors to ozone depletion in comparison to some other halogenated species. The preferred compositions of the present invention thus have the advantage of not contributing substantially to ozone depletion. The preferred compositions also do not contribute substantially to global warming compared to many of the hydrofluoroalkanes presently in use.

Preferably, the compositions of the present invention have a Global Warming Potential (GWP) of not greater than 150, more preferably not greater than 100 and even more preferably not greater than 75. As used herein, "GWP" is measured relative to that of carbon dioxide and over a 100 year time horizon, as defined in "The Scientific Assessment of Ozone Depletion, 2002, a report of the World Meteorological Association's Global Ozone Research and Monitoring Project," which is incorporated herein by reference.

The present compositions also preferably have an Ozone Depletion Potential (ODP) of not greater than 0.05, more preferably not greater than 0.02 and even more preferably about zero. As used herein, "ODP" is as defined in "The Scientific Assessment of Ozone Depletion, 2002, A report of the World Meteorological Association's Global Ozone Research and Monitoring Project," which is incorporated herein by reference.

Heat Transfer Compositions

Although it is contemplated that the compositions of the present invention may include the compounds of the present invention in widely ranging amounts, it is generally preferred that refrigerant compositions of the present invention comprise compound(s) in accordance with Formula I, and even more preferably Formula II, in an amount that is at least about 50% by weight, and even more preferably at least about 70% by weight, of the composition.

The compositions of the present invention may include other components for the purpose of enhancing or providing certain functionality to the composition, or in some cases to reduce the cost of the composition. For example, refrigerant compositions according to the present invention, especially those used in vapor compression systems, include a lubricant, generally in amounts of from about 30 to about 50 percent by weight of the composition. Furthermore, the present compositions may also include a compatibilizer, such as propane, for the purpose of aiding compatibility and/or solubility of the lubricant. Such compatibilizers, including propane, butanes and pentanes, are preferably present in amounts of from about 0.5 to about 5 percent by weight of the composition. Combinations of surfactants and solubilizing agents may also be added to the present compositions to aid oil solubility, as disclosed by U.S. Pat. No. 6,516,837, the disclosure of which is incorporated by reference. Commonly used refrigeration lubricants such as Polyol Esters (POEs) and Poly Alkylene Glycols (PAGs) that are used in refrigeration machinery with hydrofluorocarbon (HFC) refrigerants may be used with the refrigerant compositions of the present invention.

Blowing Agents, Foams and Foamable Compositions

Blowing agents may also comprise or constitute one or more of the present compositions. As mentioned above, the compositions of the present invention may include the compounds of the present invention in widely ranging amounts. It is generally preferred, however, that for preferred compositions for use as blowing agents in accordance with the present invention, compound(s) in accordance with Formula I, and even more preferably Formula II, are present in an amount that is at least about 5% by weight, and even more preferably at least about 15% by weight, of the composition.

In other embodiments, the invention provides foamable compositions, and preferably polyurethane, polyisocyanurate and extruded thermoplastic foam compositions, prepared using the compositions of the present invention. In such foam embodiments, one or more of the present compositions are included as or part of a blowing agent in a foamable composition, which composition preferably includes one or more additional components capable of reacting and/or foaming under the proper conditions to form a foam or cellular structure, as is well known in the art. The invention also relates to foam, and preferably closed cell foam, prepared from a polymer foam formulation containing a blowing agent comprising the compositions of the invention. In yet another embodiments, the invention provides a foamable composition comprising thermoplastic foams, such as polystyrene and polyethylene (PE), preferably low density PE.

In certain preferred embodiments, dispersing agents, cell stabilizers, surfactants and other additives may also be incorporated into the blowing agent compositions of the present invention. Surfactants are optionally but preferably added to serve as cell stabilizers. Some representative materials are sold under the names of DC-193, B-8404, and L-5340 which are, generally, polysiloxane polyoxyalkylene block co-polymers such as those disclosed in U.S. Pat. Nos. 2,834,748, 2,917,480, and 2,846,458, each of which is incorporated herein by reference. Other optional additives for the blowing agent mixture may include flame retardants such as tri(2-chloroethyl)phosphate, tri(2-chloropropyl)phosphate, tri(2,3-dibromopropyl)-phosphate, tri(1,3-dichloropropyl)phosphate, diammonium phosphate, various halogenated aromatic compounds, antimony oxide, aluminum trihydrate, polyvinyl chloride, and the like.

Propellant Compositions

In another aspect, the present invention provided propellant compositions comprising or consisting essentially of a composition of the present invention, such propellant composition preferably being a sprayable composition. The propellant compositions of the present invention preferably comprise a material to be sprayed and a propellant comprising, consisting essentially of, or consisting of a composition in accordance with the present invention. Inert ingredients, solvents, and other materials may also be present in the sprayable mixture. Preferably, the sprayable composition is an aerosol. Suitable materials to be sprayed include, without limitation, cosmetic materials such as deodorants, perfumes, hair sprays, cleansers, and polishing agents as well as medicinal materials such as anti-asthma and anti-halitosis medications.

Methods and Systems

The compositions of the present invention are useful in connection with numerous methods and systems, including as heat transfer fluids in methods and systems for transferring heat, such as refrigerants used in refrigeration, air conditioning and heat pump systems. The present compositions are also advantageous for in use in systems and methods of generating aerosols, preferably comprising or consisting of the aerosol propellant in such systems and methods. Methods of forming foams and methods of extinguishing and suppressing fire are also included in certain aspects of the present invention. The present invention also provides in certain aspects methods of removing residue from articles in which the present compositions are used as solvent compositions in such methods and systems.

Heat Transfer Methods

The preferred heat transfer methods generally comprise providing a composition of the present invention and causing heat to be transferred to or from the composition changing the phase of the composition. For example, the present methods provide cooling by absorbing heat from a fluid or article, preferably by evaporating the present refrigerant composition in the vicinity of the body or fluid to be cooled to produce vapor comprising the present composition. Preferably the methods include the further step of compressing the refrigerant vapor, usually with a compressor or similar equipment to produce vapor of the present composition at a relatively elevated pressure. Generally, the step of compressing the vapor results in the addition of heat to the vapor, thus causing an increase in the temperature of the relatively high pressure vapor. Preferrably, the present methods include removing from this relatively high temperature, high pressure vapor at least a portion of the heat added by the evaporation and compression steps. The heat removal step preferably includes condensing the high temperature, high pressure vapor while the vapor is in a relatively high pressure condition to produce a relatively high pressure liquid comprising a composition of the present invention. This relatively high pressure liquid preferably then undergoes a nominally isoenthalpic reduction in pressure to produce a relatively low temperature, low pressure liquid. In such embodiments, it is this reduced temperature refrigerant liquid which is then vaporized by heat transferred from the body or fluid to be cooled.

In another process embodiment of the invention, the compositions of the invention may be used in a method for producing heating which comprises condensing a refrigerant comprising the compositions in the vicinity of a liquid or body to be heated. Such methods, as mentioned hereinbefore, frequently are reverse cycles to the refrigeration cycle described above.

Foam Blowing Methods

One embodiment of the present invention relates to methods of forming foams, and preferably polyurethane and polyisocyanurate foams. The methods generally comprise providing a blowing agent composition of the present inventions, adding (directly or indirectly) the blowing agent composition to a foamable composition, and reacting the foamable composition under the conditions effective to form a foam or cellular structure, as is well known in the art. Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments of the present invention. In general, such preferred methods comprise preparing polyurethane or polyisocyanurate foams by combining an isocyanate, a polyol or mixture of polyols, a blowing agent or mixture of blowing agents comprising one or more of the present compositions, and other materials such as catalysts, surfactants, and optionally, flame retardants, colorants, or other additives.

It is convenient in many applications to provide the components for polyurethane or polyisocyanurate foams in pre-blended formulations. Most typically, the foam formulation is pre-blended into two components. The isocyanate and optionally certain surfactants and blowing agents comprise the first component, commonly referred to as the "A" component. The polyol or polyol mixture, surfactant, catalysts, blowing agents, flame retardant, and other isocyanate reactive components comprise the second component, commonly referred to as the "B" component. Accordingly, polyurethane or polyisocyanurate foams are readily prepared by bringing together the A and B side components either by hand mix for small preparations and, preferably, machine mix techniques to form blocks, slabs, laminates, pour-in-place panels and other items, spray applied foams, froths, and the like. Optionally, other ingredients such as fire retardants, colorants, auxiliary blowing agents, and even other polyols can be added as a third stream to the mix head or reaction site. Most preferably, however, they are all incorporated into one B-component as described above.

It is also possible to produce thermoplastic foams using the compositions of the invention. For example, conventional polystyrene and polyethylene formulations may be combined with the compositions in a conventional manner to produce rigid foams.

Cleaning Methods

The present invention also provides methods of removing containments from a product, part, component, substrate, or any other article or portion thereof by applying to the article a composition of the present invention. For the purposes of convenience, the term "article" is used herein to refer to all such products, parts, components, substrates, and the like and is further intended to refer to any surface or portion thereof. Furthermore, the term "contaminant" is intended to refer to any unwanted material or substance present on the article, even if such substance is placed on the article intentionally. For example, in the manufacture of semiconductor devices it is common to deposit a photoresist material onto a substrate to form a mask for the etching operation and to subsequently remove the photoresist material from the substrate. The term "contaminant" as used herein is intended to cover and encompass such a photo resist material.

Preferred methods of the present invention comprise applying the present composition to the article, with vapor degreasing and solvent cleaning methods being particularly preferred for certain applications, especially those intricate parts and difficult to remove soils. Preferred vapor degreasing and solvent cleaning methods consist of exposing an article, preferably at room-temperature, to the vapors of a boiling solvent. Vapors condensing on the object have the advantage of providing a relatively clean, distilled solvent to wash away grease or other contamination. Such processes thus have an additional advantage in that final evaporation of the present solvent composition from the object leaves behind relatively little residue as compared to the case where the object is simply washed in liquid solvent.

For applications in which the article includes contaminants that are difficult to remove, it is preferred that the present methods involve raising the temperature of the solvent composition of the present invention above ambient or to any other temperature that is effective in such application to substantially improve the cleaning action of the solvent. Such processes are also generally preferred for large volume assembly line operations where the cleaning of the article, particularly metal parts and assemblies, must be done efficiently and quickly.

In preferred embodiments, the cleaning methods of the present invention comprise immersing the article to be cleaned in liquid solvent at an elevated temperature, and even more preferably at about the boiling point of the solvent. In such operations, this step preferably removes a substantial amount, and even more preferably a major portion, of the target contaminant from the article. This step is then preferably followed by immersing the article in solvent, preferably freshly distilled solvent, which is at a temperature below the temperature of the liquid solvent in the preceding immersion step, preferably at about ambient or room temperature. The preferred methods also include the step of then contacting the article with relatively hot vapor of the present solvent composition, preferably by exposing the article to solvent vapors rising from the hot/boiling solvent associated with the first mentioned immersion step. This preferably results in condensation of the solvent vapor on the article. In certain preferred embodiments, the article may be sprayed with distilled solvent before final rinsing.

It is contemplated that numerous varieties and types of vapor degreasing equipment are adaptable for use in connection with the present methods. One example of such equipment and its operation is disclosed by Sherliker et al. in U.S. Pat. No. 3,085,918, which is incorporated herein by reference. The equipment disclosed in Sherliker et al includes a boiling sump for containing a solvent composition, a clean sump for containing distilled solvent, a water separator, and other ancillary equipment.

The present cleaning methods may also comprise cold cleaning in which the contaminated article is either immersed in the fluid composition of the present invention under ambient or room temperature conditions or wiped under such conditions with rags or similar objects soaked in solvents.

Flammability Reduction Methods

According to certain other preferred embodiments, the present invention provides methods for reducing the flammability of fluids, said methods comprising adding a compound or composition of the present invention to said fluid. The flammability associated with any of a wide range of otherwise flammable fluids may be reduced according to the present invention. For example, the flammability associated with fluids such as ethylene oxide, flammable hydrofluorocarbons and hydrocarbons, including: HFC-152a, 1,1,1-trifluoroethane (HFC-143a), difluoromethane (HFC-32), propane, hexane, octane, and the like can be reduced according to the present invention. For the purposes of the present invention, a flammable fluid may be any fluid exhibiting flammability ranges in air as measured via any standard conventional test method, such as ASTM E-681, and the like.

Any suitable amounts of the present compounds or compositions may be added to reduce flammability of a fluid according to the present invention. As will be recognized by those of skill in the art, the amount added will depend, at least in part, on the degree to which the subject fluid is flammable and the degree to which it is desired to reduce the flammability thereof. In certain preferred embodiments, the amount of compound or composition added to the flammable fluid is effective to render the resulting fluid substantially non-flammable.

Flame Suppression Methods

The present invention further provides methods of suppressing a flame, said methods comprising contacting a flame with a fluid comprising a compound or composition of the present invention. Any suitable methods for contacting the flame with the present composition may be used. For example, a composition of the present invention may be sprayed, poured, and the like onto the flame, or at least a portion of the flame may be immersed in the composition. In light of the teachings herein, those of skill in the art will be readily able to adapt a variety of conventional apparatus and methods of flame suppression for use in the present invention.

Sterilization Methods

Many articles, devices and materials, particularly for use in the medical field, must be sterilized prior to use for the health and safety reasons, such as the health and safety of patients and hospital staff. The present invention provides methods of sterilizing comprising contacting the articles, devices or material to be sterilized with a compound or composition of the present invention. Such methods may be either high or low-temperature sterilization methods. In certain embodiments, high-temperature sterilization comprises exposing the articles, device or material to be sterilized to a hot fluid comprising a compound or composition of the present invention at a temperature of from about 250° F. to about 270° F., preferably in a substantially sealed chamber. The process can be completed usually in less than about 2 hours. However, some articles, such as plastic articles and electrical components, cannot withstand such high temperatures and require low-temperature sterilization.

Low-temperature sterilization of the present invention involves the use of a compound or composition of the present invention at a temperature of from about 100 to about 200 EF. The compounds of the present invention may be combined with other common chemical sterilants, including, for example, ethylene oxide (EO), formaldehyde, hydrogen peroxide, chlorine dioxide, and ozone to form a sterilant composition of the present invention.

The low-temperature sterilization of the present invention is preferably at least a two-step process performed in a substantially sealed, preferably air tight, chamber. In the first step (the sterilization step), the articles having been cleaned and wrapped in gas permeable bags are placed in the chamber. Air is then evacuated from the chamber by pulling a vacuum and perhaps by displacing the air with steam. In certain embodiments, it is preferable to inject steam into the chamber to achieve a relative humidity that ranges preferably from about 30% to about 70%. Such humidities may maximize the sterilizing effectiveness of the sterilant which is introduced into the chamber after the desired relative humidity is achieved. After a period of time sufficient for the sterilant to permeate the wrapping and reach the interstices of the article, the sterilant and steam are evacuated from the chamber.

In the preferred second step of the process (the aeration step), the articles are aerated to remove sterilant residues. Removing such residues is particularly important in the case of toxic sterilants, although it is optional in those cases in which the substantially non-toxic compounds of the present invention are used. Typical aeration processes include air washes, continuous aeration, and a combination of the two. An air wash is a batch process and usually comprises evacuating the chamber for a relatively short period, for example, 12 minutes, and then introducing air at atmospheric pressure or higher into the chamber. This cycle is repeated any number of times until the desired removal of sterilant is achieved. Continuous aeration typically involves introducing air through an inlet at one side of the chamber and then drawing it out through an outlet on the other side of the chamber by applying a slight vacuum to the outlet. Frequently, the two approaches are combined. For example, a common approach involves performing air washes and then an aeration cycle.

EXAMPLES

The following examples are provided for the purpose of illustrating the present invention but without limiting the scope thereof.

Example 1

The coefficient of performance (COP) is a universally accepted measure of refrigerant performance, especially useful in representing the relative thermodynamic efficiency of a refrigerant in a specific heating or cooling cycle involving evaporation or condensation of the refrigerant. In refrigeration engineering, this term expresses the ratio of useful refrigeration to the energy applied by the compressor in compressing the vapor. The capacity of a refrigerant represents the amount of cooling or heating it provides and provides some measure of the capability of a compressor to pump quantities of heat for a given volumetric flow rate of refrigerant. In other words, given a specific compressor, a refrigerant with a higher capacity will deliver more cooling or heating power. One means for estimating COP of a refrigerant at specific operating conditions is from the thermodynamic properties of the refrigerant using standard refrigeration cycle analysis techniques (see for example, R. C. Downing, FLUOROCARBON REFRIGERANTS HANDBOOK, Chapter 3, Prentice-Hall, 1988).

A refrigeration/air conditioning cycle system is provided where the condenser temperature is about 150° F. and the evaporator temperature is about −35° F. under nominally isentropic compression with a compressor inlet temperature of about 50° F. COP is determined for several compositions of the present invention over a range of condenser and evaporator temperatures and reported in Table I below, based upon HFC-134a having a COP value of 1.00, a capacity value of 1.00 and a discharge temperature of 175° F.

TABLE I

| REFRIGERANT COMPOSTION | Relative COP | Relative CAPACITY | DISCHARGE TEMPERATURE (° F.) |
|---|---|---|---|
| HFO 1225ye | 1.02 | 0.76 | 158 |
| HFO trans-1234ze | 1.04 | 0.70 | 165 |
| HFO cis-1234ze | 1.13 | 0.36 | 155 |
| HFO 1234yf | 0.98 | 1.10 | 168 |

This example shows that certain of the preferred compounds for use with the present compositions each have a better energy efficiency than HFC-134a (1.02, 1.04 and 1.13 compared to 1.00) and the compressor using the present refrigerant compositions will produce discharge temperatures (158, 165 and 155 compared to 175), which is advantageous since such result will likely leading to reduced maintenance problems.

Example 2

The miscibility of HFO-1225ye and HFO-1234ze with various refrigeration lubricants is tested. The lubricants tested are mineral oil (C3), alkyl benzene (Zerol 150), ester oil (Mobil EAL 22 cc and Solest 120), polyalkylene glycol (PAG) oil (Goodwrench Refrigeration Oil for 134a systems), and a poly(alpha-olefin) oil (CP-6005-100). For each refrigerant/oil combination, three compositions are tested, namely 5, 20 and 50 weight percent of lubricant, with the balance of each being the compound of the present invention being tested The lubricant compositions are placed in heavy-walled glass tubes. The tubes are evacuated, the refrigerant compound in accordance with the present invention is added, and the tubes are then sealed. The tubes are then put into an air bath environmental chamber, the temperature of which is varied from about −50° C. to 70° C. At roughly 10° C. intervals, visual observations of the tube contents are made for the existence of one or more liquid phases. In a case where more than one liquid phase is observed, the mixture is reported to be immiscible. In a case where there is only one liquid phase observed, the mixture is reported to be miscible. In those cases where two liquid phases were observed, but with one of the liquid phases occupying only a very small volume, the mixture is reported to be partially miscible.

The polyalkylene glycol and ester oil lubricants were judged to be miscible in all tested proportions over the entire temperature range, except that for the HFO-1225ye mixtures with polyalkylene glycol, the refrigerant mixture was found to be immiscible over the temperature range of −50° C. to −30° C. and to be partially miscible over from −20 to 50° C. At 50 weight percent concentration of the PAG in refrigerant and at 60°, the refrigerant/PAG mixture was miscible. At 70° C., it was miscible from 5 weight percent lubricant in refrigerant to 50 weight percent lubricant in refrigerant.

Example 3

The compatibility of the refrigerant compounds and compositions of the present invention with PAG lubricating oils while in contact with metals used in refrigeration and air conditioning systems is tested at 350° C., representing conditions much more severe than are found in many refrigeration and air conditioning applications.

Aluminum, copper and steel coupons are added to heavy walled glass tubes. Two grams of oil are added to the tubes. The tubes are then evacuated and one gram of refrigerant is added. The tubes are put into an oven at 350° F. for one week and visual observations are made. At the end of the exposure period, the tubes are removed.

This procedure was done for the following combinations of oil and the compound of the present invention:
a) HFC-1234ze and GM Goodwrench PAG oil
b) HFC1243 zf and GM Goodwrench oil PAG oil
c) HFC-1234ze and MOPAR-56 PAG oil
d) HFC-1243 zf and MOPAR-56 PAG oil
e) HFC-1225 ye and MOPAR-56 PAG oil.

In all cases, there is minimal change in the appearance of the contents of the tube. This indicates that the refrigerant compounds and compositions of the present invention are stable in contact with aluminum, steel and copper found in refrigeration and air conditioning systems, and the types of lubricating oils that are likely to be included in such compositions or used with such compositions in these types of systems.

Comparative Example

Aluminum, copper and steel coupons are added to a heavy walled glass tube with mineral oil and CFC-12 and heated for one week at 350° C., as in Example 3. At the end of the exposure period, the tube is removed and visual observations are made. The liquid contents are observed to turn black, indicating there is severe decomposition of the contents of the tube.

CFC-12 and mineral oil have heretofore been the combination of choice in many refrigerant systems and methods. Thus, the refrigerant compounds and compositions of the present invention possess significantly better stability with many commonly used lubricating oils than the widely-used prior art refrigerant-lubricating oil combination.

What is claimed is:

1. A method of cooling air comprising:
   (a) providing a heat transfer fluid comprising at least one lubricant and a refrigerant comprising a fluoroalkene of Formula I:

$$XCF_zR_{z-3} \qquad (I)$$

where X is a $C_2$ or a $C_3$ unsaturated, substituted, alkyl radical, each substituent and each R is independently F, or H, and z is 1 to 3, provided that (i) said fluoroalkene of Formula I has at least four fluorine substituents has a terminal unsaturated carbon atom and has at least one H on said unsaturated terminal carbon, (ii) said lubricant and said refrigerant have one liquid phase at least one temperature between about −50° C. and +70° C. measured at 5% by weight of lubricant based on the weight of the refrigerant and lubricant, and (iii) said refrigerant has a Global Warming Potential (GWP) of not greater than about 75; and
   (b) cooling said air by vaporizing said refrigerant by causing heat to be transferred from the air being cooled to said heat transfer fluid.

2. The method of claim 1 wherein said fluoroalkene includes an unsaturated terminal carbon having one F substituent.

3. The method of claim 1 wherein said at least one fluoroalkene has no substantial acute toxicity as measured by inhalation exposure to mice and rats.

4. The method of claim 1 wherein z is 3.

5. The method of claim 1 wherein both substituents on the unsaturated terminal carbon are H.

6. The method of claims 1 wherein X is a $C_2$ alkyl radical.

7. The method of claim 1 further comprising providing a system having at least one compressor, at least one condenser and at least one evaporator, wherein said heat transfer fluid is in said system and said condenser is operated in a temperature range that includes about 150° F.

8. The method of claim 1 wherein said lubricant of said heat transfer fluid comprises poly alkylene glycol lubricant and wherein said at least one fluoroalkene comprises 1,3,3,3-tetrafluoropropene (HFO-1234ze).

9. The method of claim 8 wherein said lubricant is present in an amount of from about 30 to about 50% by weight of the fluid.

10. The method of claim 1 wherein said lubricant of said heat transfer fluid comprises poly alkylene glycol lubricant and wherein said at least one fluoroalkene comprises 2,3,3,3-tetrafluoropropene (HFO-1234yf).

11. The method of claim 10 wherein said lubricant is present in an amount of from about 30 to about 50% by weight of the fluid.

12. The method of claim 10 wherein said lubricant consists essentially of poly alkylene glycol.

13. The method of claim 10 wherein said heat transfer fluid has a capacity relative to HFC-134a of about 1, a Coefficient of Performance (COP) relative to HFC-134a of about 1, and a Global Warming Potential (GWP) of not greater than about 75.

14. A heat transfer method for cooling air comprising:
    (a) providing a heat transfer composition comprising at least one lubricant and a refrigerant comprising at least one fluoroalkene of Formula I:

$$XCF_zR_{3-z} \qquad (I)$$

where X is a $C_2$ or a $C_3$ unsaturated F, Cl, I or Br substituted alkyl radical, R is independently Cl, F or H, and z is 3, wherein said providing step comprises ensuring that said refrigerant does not include a fluoroalkene of Formula I which has no H substituent on an unsaturated terminal carbon, and further provided that said lubricant and said refrigerant have one liquid phase at least one temperature between about −50° C. and +70° C. measured at 5% by weight of lubricant based on the weight of the refrigerant and lubricant, and further provided that said refrigerant has a Global Warming Potential (GWP) of not greater than about 150; and
    (b) cooling air by causing heat to be transferred from the air to said refrigerant.

15. The heat transfer method of claim 14 wherein said at least one fluoroalkene has no substantial acute toxicity as measured by inhalation exposure to mice and rats.

16. The heat transfer method of claim 14 wherein z is 3.

17. The heat transfer method of claim 14 wherein both substituents on the unsaturated terminal carbon are H.

18. The heat transfer method of claim 14 wherein X is a $C_2$ alkyl radical.

19. The heat transfer method of claim 14 further comprising providing a system having at least one compressor, at least one condenser and at least one evaporator, wherein said heat transfer composition is in said system and said condenser is operated in a temperature range that includes about 150° F.

20. The heat transfer method of claim 14 wherein said lubricant of said heat transfer composition comprises poly alkylene glycol lubricant and wherein said at least one fluoroalkene consists essentially of 1,3,3,3-tetrafluoropropene (HFO-1234ze).

21. The heat transfer method of claim 20 wherein said lubricant is present in an amount of from about 30 to about 50% by weight of the composition.

* * * * *